(12) United States Patent
Biedermann et al.

(10) Patent No.: US 9,486,246 B2
(45) Date of Patent: Nov. 8, 2016

(54) BONE ANCHORING DEVICE

(75) Inventors: Lutz Biedermann, VS-Villingen (DE); Wilfried Matthis, Weisweil (DE); Gerhard Pohl, St. Georgen (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 249 days.

(21) Appl. No.: 12/969,513

(22) Filed: Dec. 15, 2010

(65) Prior Publication Data
US 2011/0152949 A1  Jun. 23, 2011

Related U.S. Application Data
(60) Provisional application No. 61/288,608, filed on Dec. 21, 2009.

(30) Foreign Application Priority Data
Dec. 21, 2009  (EP) .................................... 09180249

(51) Int. Cl.
*A61B 17/70* (2006.01)

(52) U.S. Cl.
CPC ........ *A61B 17/7037* (2013.01); *A61B 17/7035* (2013.01); *Y10T 29/49826* (2015.01)

(58) Field of Classification Search
CPC ....................... A61B 17/7035; A61B 17/7037
USPC ......... 606/264–270, 272, 305–308, 319, 328
See application file for complete search history.

(56) References Cited

U.S. PATENT DOCUMENTS

| | | |
|---|---|---|
| 5,443,467 A | 8/1995 | Biedermann et al. |
| 5,672,176 A | 9/1997 | Biedermann et al. |
| 5,716,356 A | 2/1998 | Biedermann et al. |
| 5,879,350 A * | 3/1999 | Sherman et al. ............. 606/270 |

(Continued)

FOREIGN PATENT DOCUMENTS

| | | |
|---|---|---|
| DE | 43 07 576 C1 | 4/1994 |
| EP | 0 885 598 A2 | 12/1998 |

(Continued)

OTHER PUBLICATIONS

European Search Report for European Application No. 09180249.6, European Search Report dated May 11, 2010 and mailed May 26, 2010 (9 pgs.).

*Primary Examiner* — Jan Christopher Merene
*Assistant Examiner* — Atiya Mahmud
(74) *Attorney, Agent, or Firm* — Lewis Roca Rothgerber Christie LLP

(57) ABSTRACT

A bone anchoring device includes an anchoring element including a shaft and a head; a receiving part including a first end and a second end, and having a channel for receiving a rod near the first end, and an accommodation space for accommodating the head near the second end; and a pressure element configured to be located at least partially in the accommodation space and including a flexible portion to clamp the head, wherein the anchoring element is pivotable, and the pressure element is movable inside the accommodation space to lock the head within the pressure element, and wherein a first securing portion on the pressure element and a second securing portion on the receiving part are configured to engage and form a rigid coupling therebetween to prevent removal of the pressure element from the first end of the receiving part.

20 Claims, 8 Drawing Sheets

(56) References Cited

U.S. PATENT DOCUMENTS

| | | |
|---|---|---|
| 5,882,350 A | 3/1999 | Ralph et al. |
| 7,087,057 B2* | 8/2006 | Konieczynski et al. ...... 606/278 |
| 8,048,124 B2* | 11/2011 | Chin et al. .................... 606/264 |
| 2004/0097933 A1 | 5/2004 | Lourdel et al. |
| 2005/0192571 A1 | 9/2005 | Abdelgany |
| 2005/0277927 A1* | 12/2005 | Guenther et al. ............... 606/61 |
| 2006/0264933 A1* | 11/2006 | Baker et al. .................... 606/61 |
| 2006/0276792 A1 | 12/2006 | Ensign et al. |
| 2007/0093818 A1 | 4/2007 | Biedermann et al. |
| 2007/0123862 A1 | 5/2007 | Warnick |
| 2007/0288004 A1* | 12/2007 | Alvarez .......................... 606/61 |
| 2008/0015584 A1 | 1/2008 | Richelsoph |
| 2008/0045953 A1 | 2/2008 | Garamszegi |
| 2008/0097457 A1 | 4/2008 | Warnick |
| 2008/0319490 A1* | 12/2008 | Jackson ........................ 606/308 |
| 2009/0105769 A1* | 4/2009 | Rock et al. ................... 606/308 |
| 2009/0149887 A1 | 6/2009 | Schlaepfer et al. |
| 2009/0204155 A1 | 8/2009 | Aschmann |
| 2010/0145394 A1* | 6/2010 | Harvey et al. ................ 606/302 |
| 2010/0262196 A1* | 10/2010 | Barrus et al. ................. 606/308 |
| 2012/0041490 A1* | 2/2012 | Jacob et al. .................. 606/264 |

FOREIGN PATENT DOCUMENTS

| | | |
|---|---|---|
| EP | 2 022 423 A1 | 2/2009 |
| JP | 2000-511453 A | 9/2000 |
| JP | 2001-505469 A | 4/2001 |
| TW | 200714248 | 1/2014 |
| WO | WO 98/25534 A1 | 6/1998 |
| WO | WO 98/34554 | 8/1998 |
| WO | WO 03/037199 A1 | 5/2003 |
| WO | WO 2006/116437 A2 | 11/2006 |
| WO | WO 2008/103150 A1 | 8/2008 |
| WO | WO 2009/015100 A2 | 1/2009 |

* cited by examiner

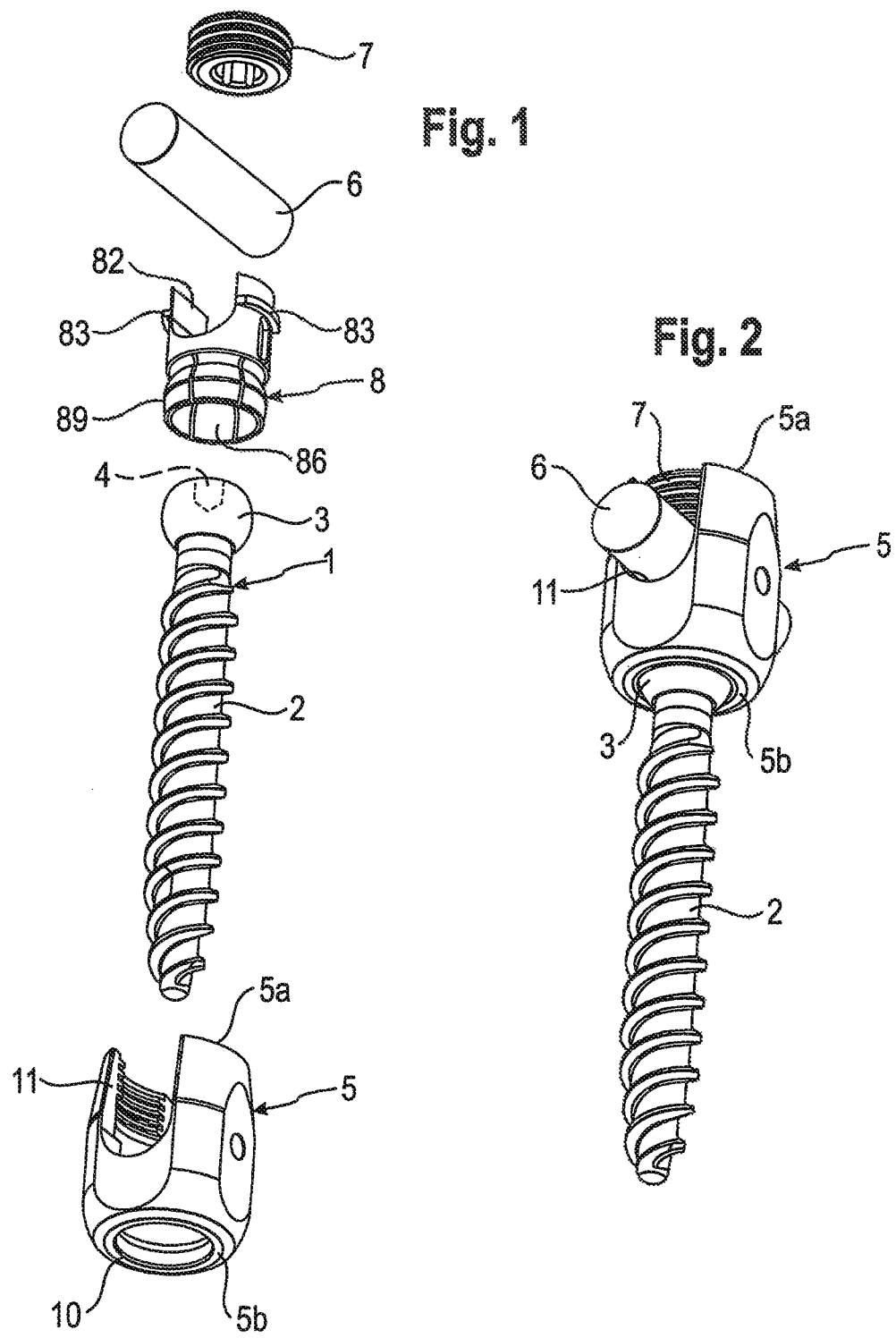

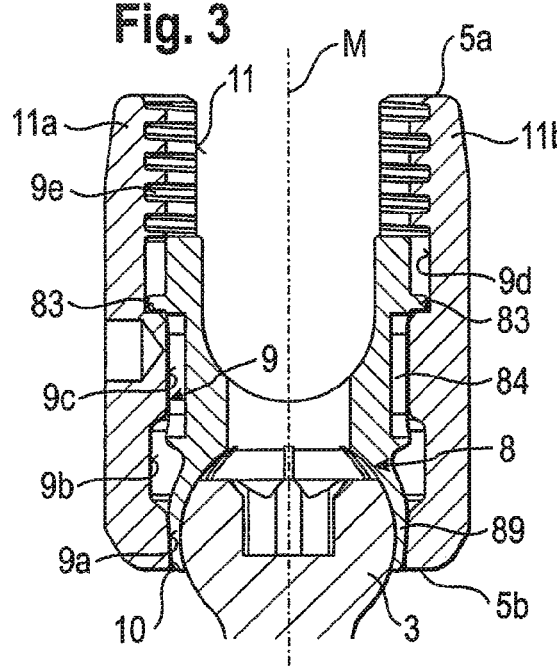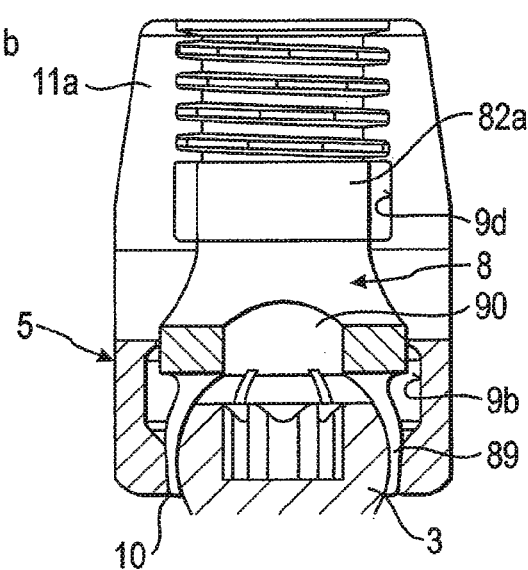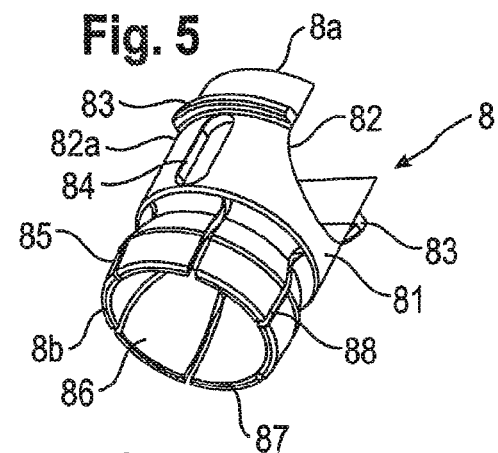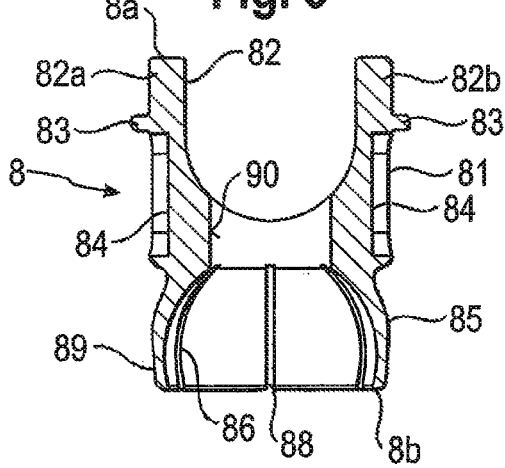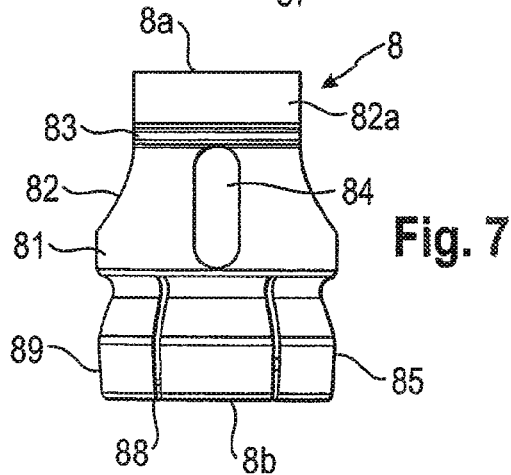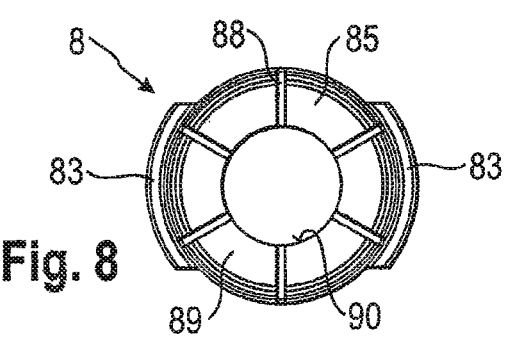

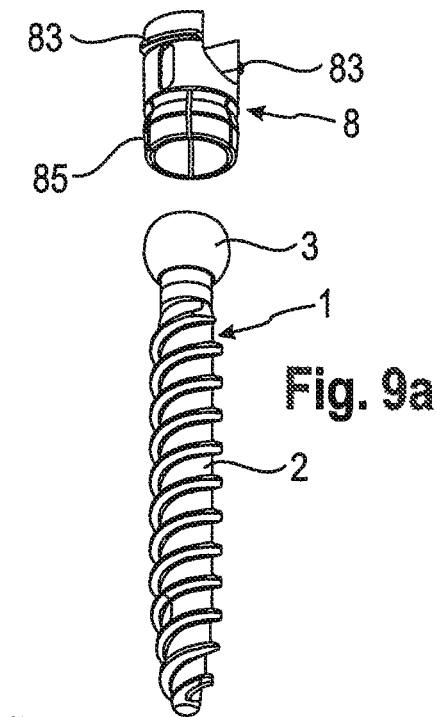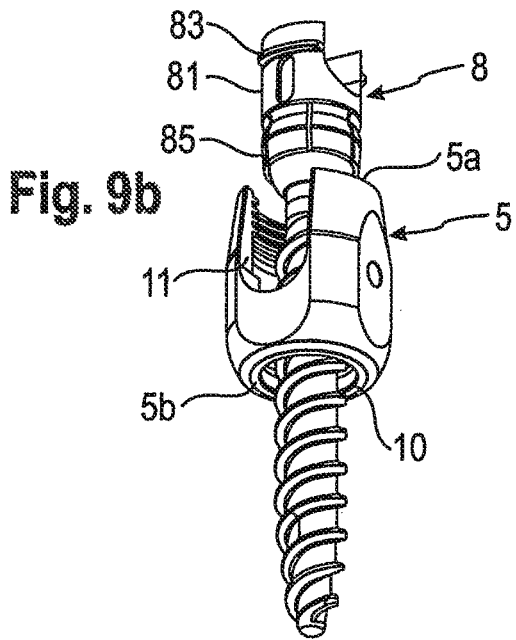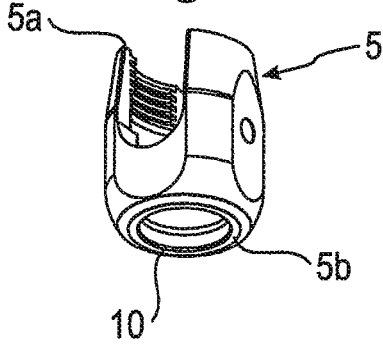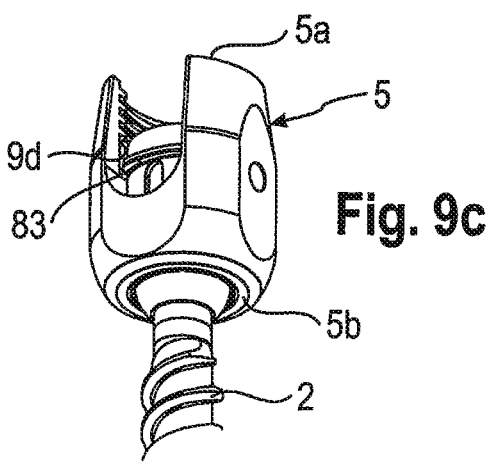

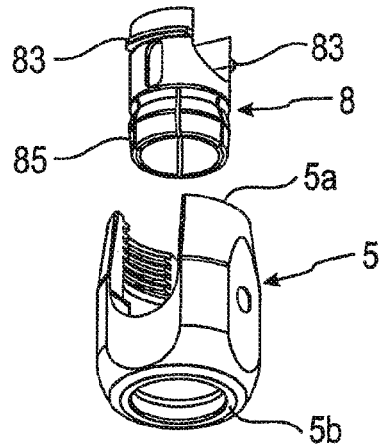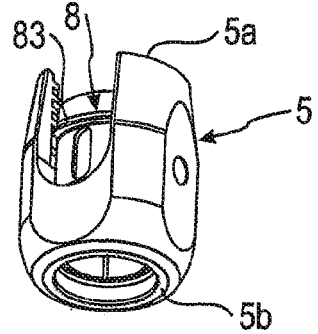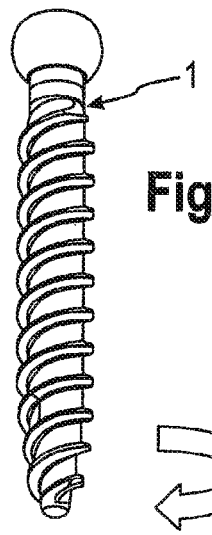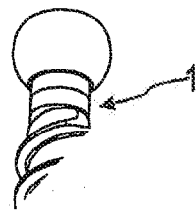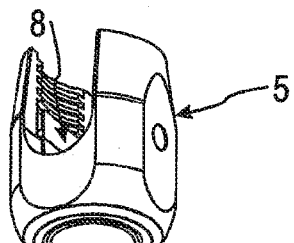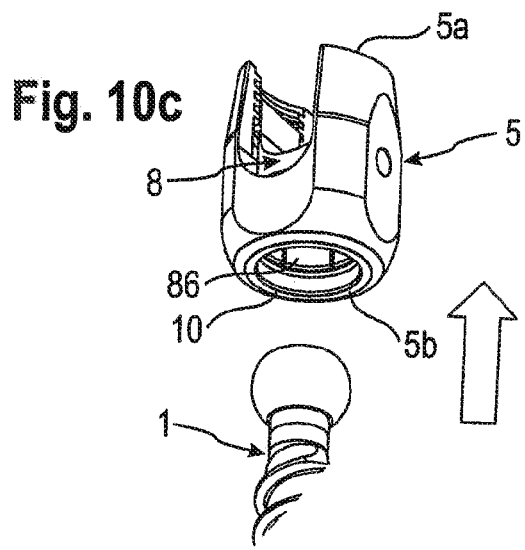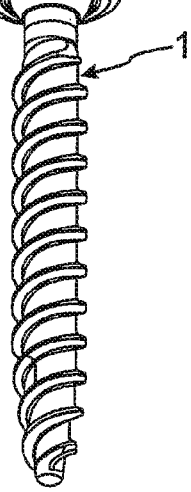
Fig. 10a
Fig. 10b
Fig. 10c
Fig. 10d

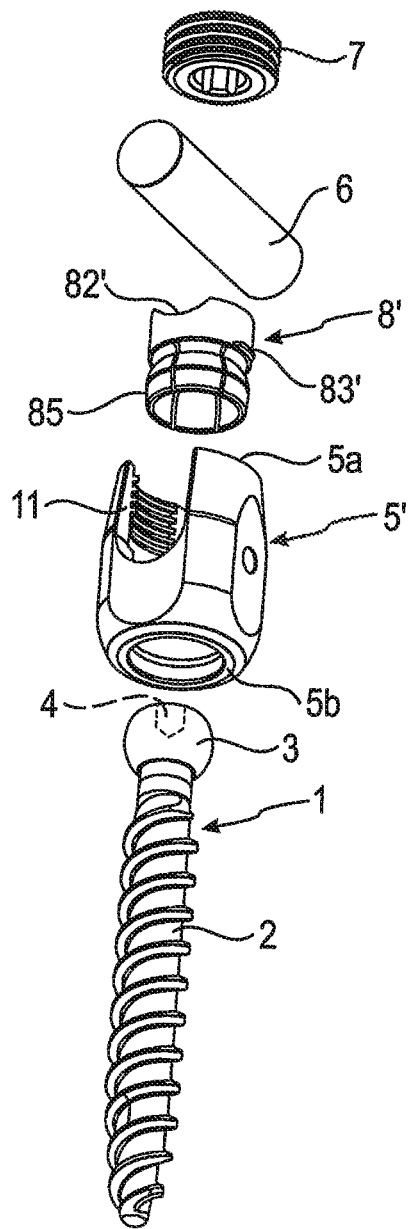
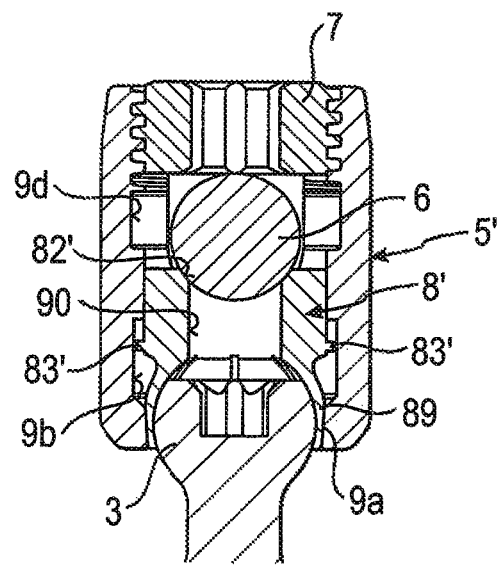

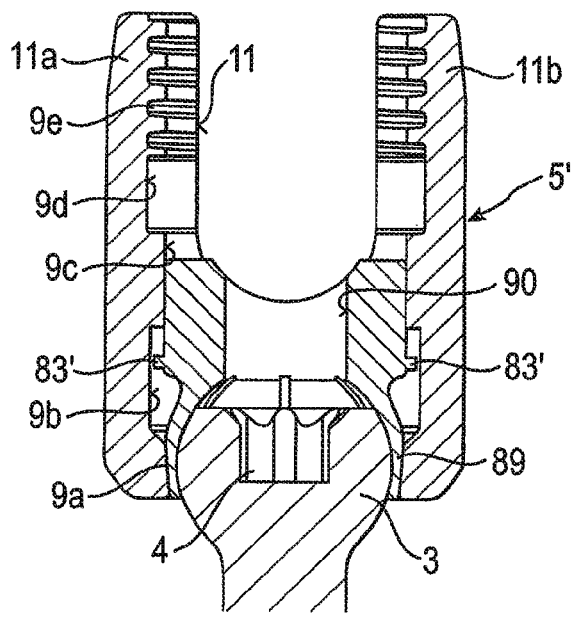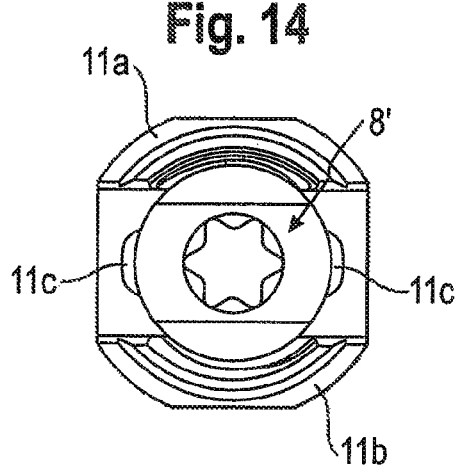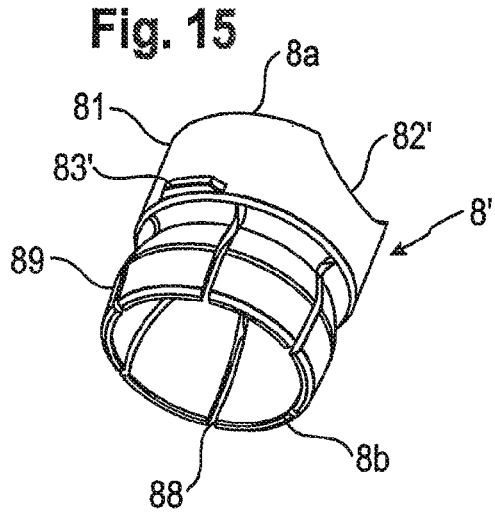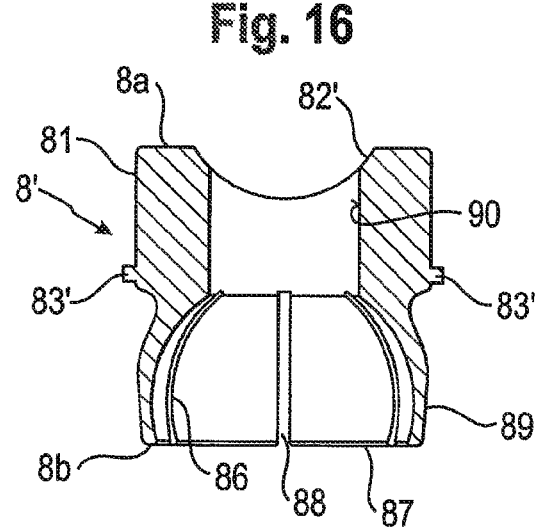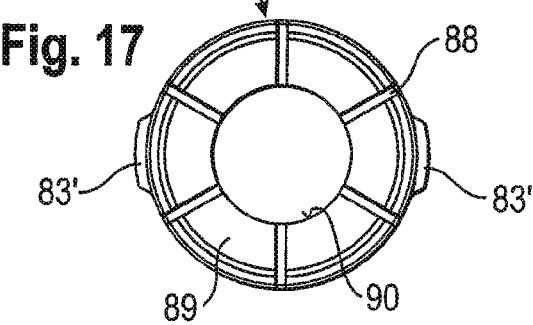

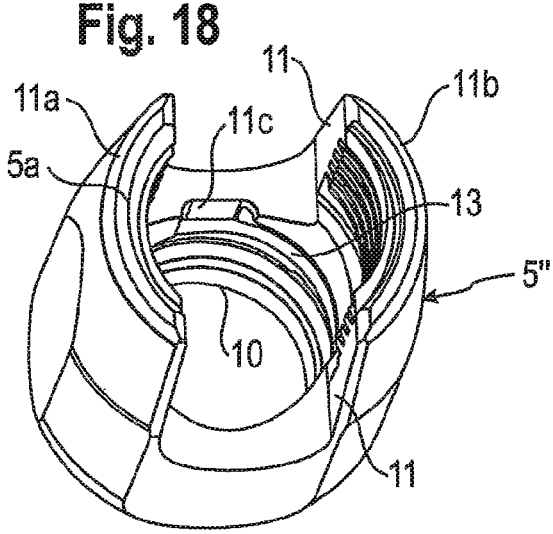
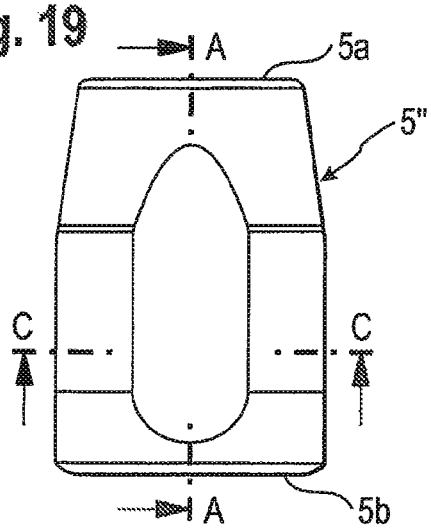
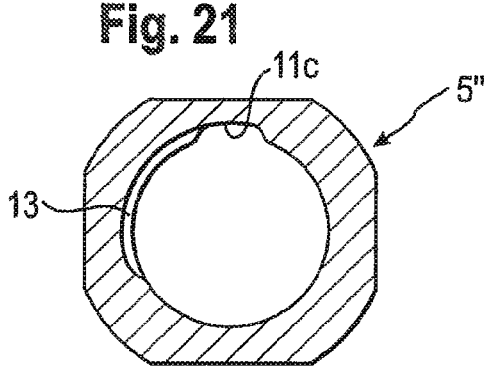
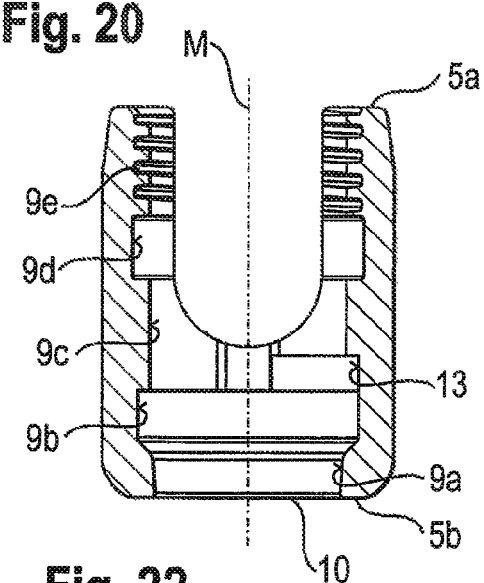
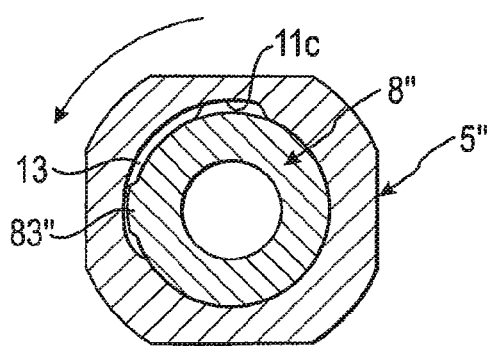
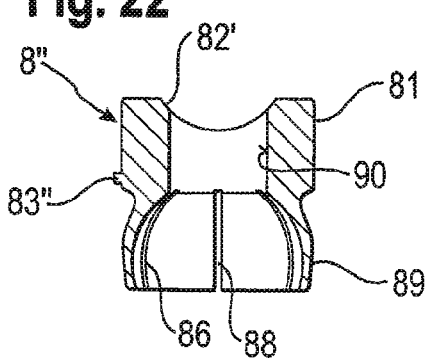

BONE ANCHORING DEVICE

CROSS-REFERENCE TO RELATED APPLICATION(S)

The present application claims the benefit of U.S. Provisional Patent Application Ser. No. 61/288,608, filed Dec. 21, 2009, the contents of which are hereby incorporated by reference in their entirety, and claims priority to European Patent Application EP 09 180 249.6, filed Dec. 21, 2009, the contents of which are hereby incorporated by reference in their entirety.

BACKGROUND

1. Field

The invention relates to a bone anchoring device for anchoring a stabilization rod in a bone or in a vertebra. The bone anchoring device includes an anchoring element, a receiving part for receiving a head of the bone anchoring element and for receiving the stabilization rod to be connected to the anchoring element. The anchoring element is pivotably connected to the receiving part and can be fixed at an angle by exerting pressure onto the head via a pressure element which is arranged in the receiving part. The pressure element has a flexible portion to clamp the head. The pressure element also has a securing portion which engages a securing portion at the receiving part to prevent a loss of the pressure element after insertion of the pressure element into the receiving part.

2. Description of Related Art

U.S. Pat. No. 5,716,356 describes a polyaxial bone screw including a screw element and a receiving part which is pivotably connected to the screw element and a pressure element to exert pressure onto the head of the screw element to fix the angle between the screw element and the receiving part. The pressure element is held in the receiving part in an aligned position by means of crimping through bores provided in the receiving part.

U.S. Pat. No. 5,672,176 describes another example of a polyaxial bone screw with a pressure element which is also held in place by crimp bores without impeding a sufficient movement of the pressure element to clamp the head.

WO2006/116437 A2 describes a bone anchor for spinal fixation in the form of a polyaxial bone screw including a screw element, a housing, a sleeve and a collet arranged in the housing for exerting pressure onto the head of the screw element. The sleeve has retention tabs which snap into slots in opposite wall positions of the housing.

The polyaxial bone screw described in DE 43 07 576 C1 has an inner thread at the receiving part which engages an outer thread of the pressure element as well as an outer thread of a clamping screw which clamps the head. WO98/34554 describes a multi-axial bone engaging fastener assembly wherein a crown member presses onto the head of the bone screw. The crown member is threaded and inserted by threading it through the threaded portion of the receiver member. Therefore, it cannot escape inadvertently.

Usually, the polyaxial bone anchoring devices of the above described types are provided, for example, by the manufacturer, in a pre-assembled condition. In this condition a specific screw element, for example, a screw element having a specific length and a specific shaft diameter or specific thread form is connected to the receiving part, and the pressure element is arranged therein so that it cannot fall out. For surgery, the necessary number and types of such pre-assembled polyaxial bone screws are selected and provided in advance as a full set of implants.

SUMMARY

Embodiments of the invention provide a bone anchoring device, wherein parts can be selected and assembled by the surgeon or by any other personnel in a simple manner at the operation site, or at any other place after the parts have been manufactured. In addition, the bone anchoring device provides for improved handling during surgery.

The bone anchoring device has few parts. The parts are of a simple design. This provides for lower costs of manufacturing and convenient handling. The bone anchoring device can be assembled at any point after the parts have been manufactured and before the screw element is inserted into the bone. Therefore, assembling of the polyaxial bone screw can be carried out by anybody, in particular by the surgeon or by any personnel assisting him before or during surgery.

With such a bone anchoring device, a modular system can be provided which allows for combinations of various anchoring elements with any suitable receiver on demand, depending on actual clinical requirements and situations. This reduces the costs of polyaxial screws, reduces inventory, and gives the surgeon a substantial choice of implants. In addition, existing receiving parts may be upgraded to form the bone anchoring device according to embodiments of the invention.

The pressure element of the bone anchoring device is secured against falling out (i.e., loss of the pressure element). The coupling between the receiving part and the pressure element is implemented by a rigid coupling, which is easier to manufacture than a spring based coupling. The screw element can be assembled from the top of the receiving part or from the bottom of the receiving part. This gives the surgeon using the bone anchoring device substantial freedom with respect to application of the bone anchoring device.

BRIEF DESCRIPTION OF THE DRAWINGS

Further features and advantages of the invention will become apparent from the description of embodiments by means of the accompanying drawings. In the drawings:

FIG. 1 shows an exploded perspective view of a bone anchoring device according to a first embodiment;

FIG. 2 shows the bone anchoring device of FIG. 1 in an assembled state;

FIG. 3 shows a cross-sectional view of the bone anchoring device according to the first embodiment, the cross-section taken perpendicular to a rod axis;

FIG. 4 shows a cross-sectional view of the bone anchoring device according to the first embodiment, the cross-section taken along the rod axis;

FIG. 5 shows a perspective view of a pressure element of the bone anchoring device according to the first embodiment;

FIG. 6 shows a cross-sectional view of the pressure element, the cross-section taken perpendicular to the rod axis;

FIG. 7 shows a side view of the pressure element of FIG. 5 seen in a direction perpendicular to the rod axis;

FIG. 8 shows a bottom view of the pressure element of FIG. 5;

FIGS. 9a to 9d show steps of assembling the bone anchoring device according to the first embodiment in a first sequence;

FIGS. 10a to 10d show steps of assembling the bone anchoring device according to the first embodiment in a second sequence;

FIG. 11 shows an exploded perspective view of a bone anchoring device according to a second embodiment;

FIG. 12 shows a cross-sectional view of the bone anchoring device according to the second embodiment in an assembled state, the cross-section taken perpendicular to a rod axis;

FIG. 13 shows an enlarged cross-sectional view of the second embodiment as shown in FIG. 12 without the rod and the fixation screw;

FIG. 14 shows a top view of the bone anchoring device according to the second embodiment;

FIG. 15 shows a perspective view of a pressure element of the bone anchoring device according to the second embodiment;

FIG. 16 shows a cross-sectional view of the pressure element of FIG. 15, the cross-section taken perpendicular to the rod axis;

FIG. 17 shows a bottom view of the pressure element of FIG. 15;

FIG. 18 shows a perspective view from the top of a receiving part of the bone anchoring device according to a modification of the second embodiment;

FIG. 19 shows a side view perpendicular to the rod axis of the receiving part of FIG. 18;

FIG. 20 shows a cross-sectional view of the receiving part of FIG. 18, the cross-section taken along line A-A of FIG. 19;

FIG. 21 shows a cross-sectional view from the top of the receiving part of FIGS. 18 and 19, the cross-section taken along plane C in FIG. 19;

FIG. 22 shows a cross-sectional view of the pressure element of the modified second embodiment;

FIG. 23 shows a cross-sectional view of the receiving part and the inserted pressure element, the cross-section taken along plane C in FIG. 19;

DETAILED DESCRIPTION

Figure 24:
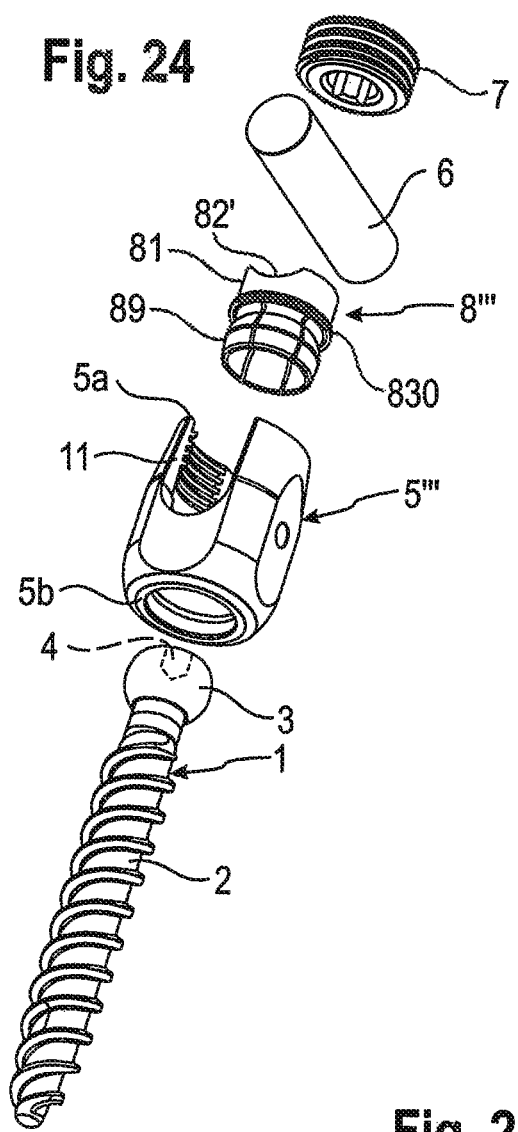
FIG. 24 shows an exploded perspective view of the bone anchoring device according to a third embodiment.

As shown in FIGS. 1 and 2, a bone anchoring device according to a first embodiment includes a bone anchoring element 1 in the form of a bone screw having a threaded shaft 2 and a head 3, which in this embodiment is a spherical segment-shaped head. The head 3 has a recess 4 for engagement with a screwing-in tool. The bone anchoring device further includes a receiving part 5 for receiving a rod 6 to connect the rod to the bone anchoring element 1. Further, a fixation element 7 in the form of an inner screw or set screw is provided for securing and clamping the rod 6 in the receiving part 5. In addition, the bone anchoring device includes a pressure element 8 for exerting pressure to lock the head 3 in the receiving part 5.

The receiving part 5 is explained with reference to FIGS. 1 to 4. The receiving part 5 includes a first end which may be characterized as a top end 5a and a second end which may be characterized as a bottom end 5b, and an axis of symmetry M passes through the top end 5a and the bottom end 5b. A bore 9 which is coaxial with the axis of symmetry M extends from the top end 5a to the bottom end 5b. By means of the bore 9, an opening 10 is provided at the bottom end. The diameter of the bore 9, and therefore the diameter of the opening 10 at the bottom end 5b, is greater than a greatest outer diameter of the head 3. Adjacent the bottom end 5b, the bore 9 has a narrowing section 9a, which narrows towards the bottom end 5b. The narrowing section can have a taper or a rounded portion or any other shape which provides exertion of a compression force onto a pressure element 8 which is described below. The narrowing section 9a also provides a seat for the screw head 3 with the pressure element 8. The bore 9 further includes in the lower portion of the receiving part 5 a section 9b with an enlarged diameter, and following or adjacent to this a middle section 9c with a reduced diameter which is still greater than the largest diameter of the head 3. Following or adjacent to the reduced diameter middle section 9c, a recessed section 9d with an enlarged diameter is formed, which serves as a securing portion for engagement with the pressure element 8. Between the recessed section 9d and the top end 5a there is a section 9e which is provided with an internal thread. The diameter of the section 9e is smaller than the diameter of the section 9d and slightly smaller than the largest outer diameter of the pressure element 8, but still greater than the outer diameter of the head 3.

In a region adjacent to the top end 5a the receiving part 5 has a substantially U-shaped recess 11, which is symmetric with respect to the symmetry axis M. The recess 11 has a bottom which is directed towards the bottom end 5b, and provides for two free lateral legs 11a, 11b extending towards the top end 5a. The channel formed by the substantially U-shaped recess 11 is sized so as to receive a rod 6 therein, which can connect a plurality of anchoring devices.

As can be seen in particular in FIGS. 3 and 4, the recessed section 9d is located on the inner wall of the legs 11a, 11b. The recessed section 9d cooperates with a portion of the pressure element 8, to prevent escaping of the pressure element 8 from the receiving part 5.

As can be seen in FIGS. 1 and 3 to 8, the pressure element has a top end 8a and a bottom end 8b. Adjacent to the top end 8a there is a substantially cylindrical first section 81 which has an outer diameter which is slightly smaller than the inner diameter of the middle section 9c of the bore 9, so that the pressure element 8 can extend, with at least a part of its cylindrical section 81, through the middle section 9c of the receiving part 5. Adjacent to the top end 8a, a substantially U-shaped recess 82, is provided which is formed to guide the rod 6 therein. By means of the substantially U-shaped recess 82, a channel with side walls 82a, 82b is formed. At a distance from the top end 8a on each side wall 82a, 82b, a projection 83 is formed which extends from the outer wall in a circumferential direction along the side walls 82a, 82b. The outer diameter of the projection 83 is greater than the inner diameter of the middle section 9c of the bore 9 and greater than the inner diameter of the threaded section 9e of the receiving part 5, but slightly smaller than the inner diameter of the recessed section 9d, so that the projection 83 can engage the recessed section 9d. Hence, the projection 83 forms a securing portion which cooperates with the recessed section 9d to prevent loss of the pressure element 8 from the receiving part 5. The width of the side walls 82a, 82b of the channel as can be seen in FIG. 7, is at least slightly smaller than the width of the substantially U-shaped recess 11 of the receiving part 5. The pressure element 8 has a further recess 84 in the outer wall of each side wall 82a, 82b which is located on the side of the projection facing away (e.g., farther away) from the top end 8*a* and which can serve, for example for engagement with a tool (not shown).

The pressure element 8 further has a second section 85 which has a hollow interior 86 which is substantially spherically-shaped and is sized to clamp the spherical head 3 therein. A greatest outer diameter of the second section 85 is substantially the same as the outer diameter of the cylindrical first section 81. A free end of the second section 85 provides an opening 87 for the introduction of the head 3. Further, the second section 85 includes a plurality of slits 88 extending from the opening 87 through the second section 85 to define or form a resilient wall. The number and the dimension of the slits 88 is such that the wall of the second portion 85 is flexible enough to snap onto the head 3 when the head 3 is being inserted. The slits 88 may extend into the first cylindrical section 81 (not shown) to enhance flexibility. The outer surface of the second section 85 is substantially rounded and has tapered or curved or otherwise narrowing portion 89 towards the bottom end 8*b*. The narrowing portion 89 cooperates with the narrowing portion 9*a* of the receiving part 5 when the head is being locked in the receiving part 5.

The fixation element 7 is in this embodiment an inner screw which is configured to press onto the rod 6 when it is screwed-in between the legs 11*a*, 11*b* of the receiving part 5. It should be noted that in the embodiment shown the side walls 82*a*, 82*b* extend below the rod surface when the rod 6 is inserted. Hence, by tightening the inner screw 7, pressure is also exerted onto the pressure element 8, and therefore onto the head 3. However, any other closure and fixation mechanism is conceivable. For example, the fixation element 7 can be a two-part fixation element having an outer screw pressing onto the top end of the pressure element and an inner screw which independently presses onto the rod for independent rod and head fixation.

The section 9*e* of the receiving part having the internal thread is shown with a flat thread in the figures. However, any other thread form may instead be implemented. Specific closure and fixation mechanisms adapted to a specific thread form may then be utilized.

The parts of the bone anchoring device are made of a body compatible material, in particular of a body compatible metal, metal alloy or body compatible plastics. For example, materials like stainless steel, titanium, nickel titanium alloys, such as Nitinol, body compatible plastics such as polyether ether ketone (PEEK) or combinations thereof may be used.

The steps of assembling the bone anchoring device according to a first sequence are now described with reference to FIGS. 9*a* to 9*d*. In a first step shown in FIG. 9*a* a specific bone anchoring element 1 which is suitable for the intended clinical application is provided. It can be selected from a plurality of bone anchoring elements having different shaft lengths, shaft diameters etc. Usually the heads 3 of the bone anchoring elements have approximately the same size. The receiving part 5 and the pressure element 8 are provided. Then the pressure element 8 is first assembled with the screw element 1. That means, the head 3 is inserted through the opening 87 into the hollow interior section 86 of the pressure element 8. By means of the flexible wall sections, the pressure element 8 is easily snapped onto the head 3.

Then, as shown in FIG. 9*b* the bone anchoring element 1 with the pressure element 8 mounted thereon is inserted from the top end 5*a* into the receiving part 5. The orientation of the pressure element 8 relative to the receiving part 5 is such that the projections 83 point in the direction of (e.g., aligned with) the U-shaped recess. As shown in FIG. 9*c* the bone anchoring element 1 with the pressure element 8 mounted thereon is then further inserted into the receiving part 5 with the projection 83 of the pressure element 8 being located within the U-shaped recess 11.

Then, as shown in FIG. 9*d* in connection with FIGS. 3 and 4 the bone anchoring element 1 together with the pressure element 8 is rotated by 90° such that the projection 83 on either side of the side walls of the pressure element 8 engages the recessed section 9*d* on either side of the legs 11*a* and 11*b* of the receiving part 5. When the projection 83 engages the recessed section 9*d*, the pressure element 8 is prevented from falling out, since the projection 83 is hindered by the upper edge of the recessed section 9*d* acting as a stop. Further, the pressure element 8 is prevented from being inserted too deeply, since the lower edge of the recessed section 9*d* adjacent to middle section 9*c* also acts as a stop. In this position, which is shown in FIGS. 3 and 4 the flexible second section 85 of the pressure element 8 is compressed by the narrowing portion 9*a* of the receiving part 5 to clamp the head 3.

Further, as can be seen in FIG. 9*d*, the substantially U-shaped recesses of the pressure element 8 and the receiving part 5 are aligned by rotation of the pressure element 8.

According to the first sequence of steps of assembly described above, the bone anchoring device is used as a top loading polyaxial bone anchoring device (i.e. the bone anchoring element 1 is introduced from the top end 5*a* of the receiving part 5).

In clinical use, the surgeon or any other personnel, for example assistant personnel, can select a suitable bone anchoring element and assemble the polyaxial bone anchoring device by himself using, for example, simple tools. After assembly, the bone anchoring element is inserted into a bone and the receiving part 5 is aligned with a stabilization rod 6 which connects several bone anchoring devices. To fix the rod 6 to the bone anchoring element, a fixation element 7 is tightened. By tightening the fixation element, the narrowing portion 89 of the pressure element 8 is further pressed into the narrowing section 9*a* of the receiving part 5 so that after final tightening the head 3 is clamped firmly, so that it is locked in a particular angular position with respect to the receiving part 5. Due to the design of the pressure element 8 and the receiving part 5, depending on the specific geometry of the narrowing portion 85 of the pressure element 8 and the narrowing section 9*a* of the receiving part 5, a self-locking of the head 3 may occur before final locking. A self-locking can occur, for example, if the sections 9*a* and 89 have a taper with an appropriate cone angle for friction-locking. The self-locking may be of use in some clinical application where it is desirable to maintain an angular relation between the screw element and the receiving part before final locking.

The assembly of the bone anchoring device according to a second alternative sequence of steps is now described with reference to FIGS. 10*a* to 10*d*. As shown in FIGS. 10*a* and 10*b*) first, the pressure element 8 is inserted from the top end 5*a* into the receiving part 5. The projection 83 points into the U-shaped recess 11 of the receiving part 5. Then, as shown in FIG. 10*c* the pressure element 8 is rotated by 90° such that the projection 83 engages the recessed portion 9*d*. In this position, the pressure element 8 is prevented from escaping through the top end 5*a*. Further, the U-shaped recesses of the pressure element 8 and the receiving part 5 are aligned. Then, the bone anchoring element 1 is inserted through the opening 10 at the bottom end 5*b* of the receiving part 5, and inserted into the flexible second portion 85 of the pressure element 8, as shown in FIG. 10*d*. Thereby, the pressure element 8 is moved towards the top end 5*a* of the receiving part 5 until the projection 83 abuts against an upper edge of the recess 9*d*, which acts as a stop. The flexible section of the pressure element 8 can widen into the space provided by the section 9*b* of the bore 9 to snap onto the head 3.

In the manner described above the bone anchoring device can be used as a bottom loading polyaxial bone anchoring device, wherein the bone anchoring element 1 is introduced into the receiving part 5 from the bottom end 5*b*. In clinical use, the bone anchoring element 1 may first be inserted into the bone, and the receiving part 5 with pressure element 8 therein may then be mounted on the bone anchoring element 1.

A second embodiment of the bone anchoring device is described with reference to FIGS. 11 to 17. Parts which are similar to the first embodiment are indicated with the same reference numerals and the descriptions thereof are not repeated. The second embodiment differs from the first embodiment in the design of the pressure element and the receiving part. The pressure element 8' has instead of the channel provided by the U-shaped recess 82 only a groove 82' in which the rod 6 rests. At the lower end of the cylindrical portion 81 which faces away from (e.g., opposite to) the top end 8*a*, two projections 83' which are offset at 90° from the groove 82' are provided. As shown in FIG. 12, when the bone anchoring device is assembled and the fixation element 7 is tightened, the projections 83' extend into the enlarged diameter section 9*b* in the lower portion of the receiving part 5'. An upper edge of this portion 9*b* forms a stop for the projection 83' which prevents escaping of the pressure element 8' through the top end 5*a* when the rod 6 and the fixation element 7 are not inserted, as shown in FIG. 13.

To allow the insertion of the pressure element 8' into the receiving part 5' and engagement of the projections 83', the receiving part 5' has on the bottom of its substantially U-shaped recess 11 two recesses 11*c*, which are positioned and sized such that the projections 83' can engage therewith (e.g., pass through) during insertion of the pressure element 8'.

The assembly of the bone anchoring device is similar to that of the first embodiment. The pressure element 8' alone or the pressure element 8' with the bone anchoring element 1 mounted therein is inserted into the receiving part 5' with the projections 83' pointing into the U-shaped recess 11 of the receiving part 5'. The pressure element 8' is moved in the direction towards the bottom end 5*b* of the receiving part 5' until the projections 83' engage the recesses 11*c* on the bottom of the substantially U-shaped recess 11. After further insertion, when the projections 83' reach the section 9*b* with the enlarged diameter, the pressure element 8' is rotated by 90° so that its groove 82' is aligned with the U-shaped recess 11 of the receiving part 5'. In this condition, the pressure element 8' is secured against falling out.

A modification of the second embodiment is now described with reference to FIGS. 18 to 23. It differs from the second embodiment in that the pressure element 8" has only one projection 83", instead of two projections 83' as in the second embodiment. Correspondingly, the receiving part 5" of the modified second embodiment has only one recess 11*c* on the bottom of the substantially U-shaped recess 11 for engagement with the only one projection 83". Further, as shown in FIGS. 18, 20 and 21, a recess 13 is provided which extends from the recess 11*c* in a circumferential direction substantially for a quarter circle length. Hence, the projection 83" of the pressure element 8" is guided in the recess 13 when the pressure element 8" is rotated to align the U-shaped recesses. The projection 83" abuts against the upper edge of the recess 13 which acts as a stop. Further, the projection 83" abuts against the end of the recess 13 in a circumferential direction, which prevents further rotation of the pressure element 8" as shown in FIG. 23.

Figure 25:
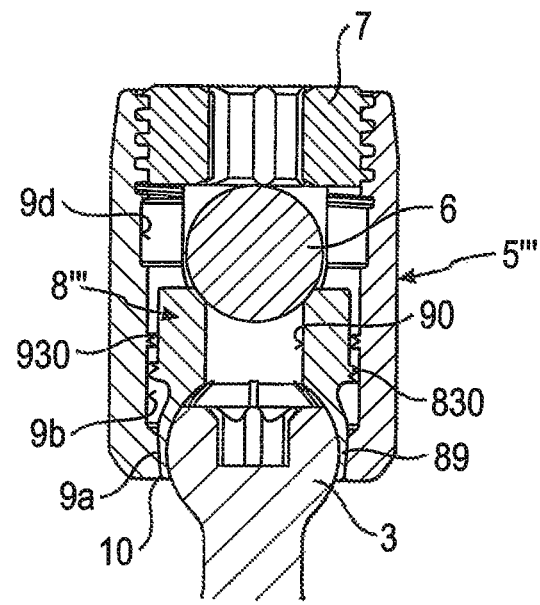
FIG. 25 shows a cross-sectional view of the bone anchoring device according to the third embodiment in an assembled state, the cross-section taken perpendicular to a rod axis.
Figure 26:
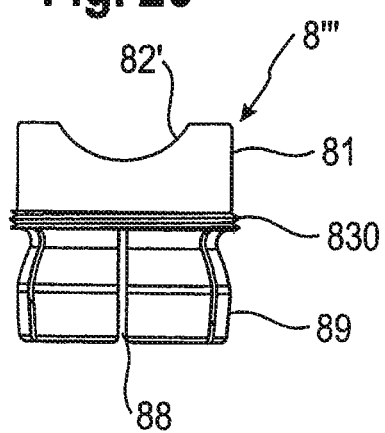
FIG. 26 shows a side view of a pressure element according to the third embodiment.

A third embodiment of the bone anchoring device will now be described with reference to FIGS. 24 to 26.

The third embodiment differs from the first and the second embodiment in the design of the pressure element and the receiving part. In the third embodiment, a coupling between the pressure element 8''' and the receiving part 5''' which prevents the falling out of the pressure element 8''' is a threaded coupling. Parts of the receiving part 5''' and the pressure element 8''' according to the third embodiment which are similar to those of the first and second embodiments are indicated with the same reference numerals, and the descriptions thereof are not repeated. The pressure element 8''' differs from the pressure elements according to the second embodiment in that instead of the projections 83'/83" a section 830 with a fine thread is provided at a lower end of the substantially cylindrical section 81. The height of the section 830 in an axial direction is small compared to the height of the substantially cylindrical section 81. The thread can be for example a metric fine thread or any other thread.

The receiving part 5''' has, instead of the portion 9*c* with the reduced diameter of the bore 9 according to the bone anchoring devices of the first and second embodiments, a corresponding threaded section 930 of the bore 9 which cooperates with the threaded section 830 of the pressure element 8'''.

When the pressure element 8''' is inserted into the receiving part 5''' and the threaded section 830 is screwed through the threaded section 930 with the internal thread so that it enters the enlarged diameter section 9*b*, the section 930 having the internal thread acts as a stop which prevents escape of the pressure element 8''' through the top end 5*a*. As in the first and second embodiments, the securing against falling out is achieved by first inserting the pressure element 8''' and then rotating it. In the third embodiment the rotation is realized by screwing the pressure element 8''' through the section 930 with the internal thread.

Further modifications of the bone anchoring device are conceivable. For example, instead of the pressure element having the projections as described in the first and second embodiments, the receiving part can instead have the projections, which engage in corresponding recesses provided at the pressure element.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

The invention claimed is:

1. A bone anchoring device comprising:
    an anchoring element comprising a shaft for anchoring in a bone, and a head;
    a receiving part comprising a first end and a second end, and having a channel for receiving a rod at the flat the first end, and an accommodation space for accommodating the head, the accommodation space having an opening at the second end; and
    a pressure element configured to be located at least partially in the accommodation space, the pressure element comprising a flexible portion configured to be positioned around a portion of the head having a greatest diameter to clamp the head therein, wherein the anchoring element is pivotable with respect to the receiving part, and the pressure element is movable inside the accommodation space to lock the head within the flexible portion of the pressure element and to fix the anchoring element at an angle relative to the receiving part, wherein the pressure element comprises a first securing portion, and the receiving part comprises a second securing portion configured to engage the first securing portion, wherein when the head of the anchoring element is in the flexible portion of the pressure element and while the pressure element maintains a first rotational orientation relative to the receiving part, the pressure element is movable axially from the first end of the receiving part to a first axial position wherein the first securing portion of the pressure element is closer than the second securing portion of the receiving part is to the second end of the receiving part, and wherein when the pressure element is at the first axial position, the pressure element is rotatable between the first rotational orientation wherein the first securing portion is out of engagement with the second securing portion, and a second rotational orientation wherein the first securing portion is engaged with the second securing portion to form a rigid coupling therebetween to prevent removal of the pressure element from the first end of the receiving part.

2. The bone anchoring device according to claim 1, wherein the receiving part has near the opening a narrowing portion configured to cooperate with a corresponding portion of the pressure element to clamp the head.

3. The bone anchoring device according to claim 2, wherein one of the narrowing portion of the receiving part or the corresponding portion of the pressure element is tapered, and the other one of the narrowing portion of the receiving part or the corresponding portion of the pressure element is tapered or curved.

4. The bone anchoring device according to claim 1, wherein the pressure element is insertable into the receiving part only from the first end.

5. The bone anchoring device according to claim 1, wherein the bone anchoring element is insertable into the receiving part from the first end or the second end.

6. The bone anchoring device according to claim 1, wherein when the first securing portion and the second securing portion are engaged, the second securing portion provides a stop to prevent the removal of the pressure element from the first end.

7. The bone anchoring device according to claim 1, wherein the first securing portion comprises a projection at an outer wall of the pressure element, and the second securing portion includes a recess at an inner wall of the receiving part.

8. The bone anchoring device according to claim 1, wherein the pressure element has a substantially cylindrical portion, and wherein the first securing portion is provided near a first end of the pressure element, wherein the first end of the pressure element is arranged to be closer than a second end of the pressure element to the first end of the receiving part.

9. The bone anchoring device according to claim 1, wherein the pressure element comprises a first substantially cylindrical section and a second section comprising the flexible portion having at least one flexible wall portion configured to be compressed around the head to clamp the head.

10. The bone anchoring device according to claim 1, wherein the pressure element is formed in one piece.

11. The bone anchoring device according to claim 1, wherein the opening of the accommodation space is sized for introduction of the head from the second end.

12. The bone anchoring device according to claim 1, wherein the first securing portion and the second securing portion are shaped such that the rigid coupling comprises a positive fit between the first securing portion and the second securing portion.

13. A modular system comprising:
a plurality of anchoring elements each comprising a shaft for anchoring in a bone, and a head, wherein the anchoring elements have different shafts and/or different heads from one another;
a plurality of different receiving parts each comprising a first end and a second end, and having a channel for receiving a rod at the first end, and an accommodation space for accommodating the head, the accommodation space having an opening at the second end; and
a plurality of different pressure elements each configured to be located at least partially in the accommodation space of a corresponding one of the receiving parts, a first pressure element from among the pressure elements comprising a flexible portion configured to receive the head of at least a first anchoring element from among the anchoring elements and to be positioned around a portion of the head having a greatest diameter to clamp the head therein,
wherein when the head of the first anchoring element is introduced into a first receiving part from among the receiving parts that corresponds to the first pressure element, the first anchoring element is pivotable with respect to the first receiving part, and the first pressure element is movable inside the accommodation space to lock the head within the flexible portion of the first pressure element and to fix the first anchoring element at an angle relative to the first receiving part;
wherein the first pressure element comprises a first securing portion, and the first receiving part comprises a second securing portion configured to engage the first securing portion,
wherein when the head of the first anchoring element is in the flexible portion of the first pressure element and while the first pressure element maintains a first rotational orientation relative to the first receiving part, the first pressure element is movable axially from the first end of the first receiving part to a first axial position wherein the first securing portion of the first pressure element is closer than the second securing portion of the first receiving part is to the second end of the first receiving part, and
wherein when the first pressure element is at the first axial position, the first pressure element is rotatable between the first rotational orientation wherein the first securing portion is out of engagement with the second securing portion, and a second rotational orientation wherein the first securing portion is engaged with the second securing portion to form a rigid coupling therebetween to prevent removal of the first pressure element from the first end of the first receiving part .

14. A method for coupling a rod to an anchoring element via a bone anchoring device, the bone anchoring device comprising a receiving part comprising a first end and a second end and having a channel for receiving the rod at the first end and an accommodation space for accommodating a head of the anchoring element, the accommodation space having an opening at the second end, and a pressure element configured to be located at least partially in the accommodation space, the pressure element comprising a flexible portion configured to be positioned around a portion of the head having a greatest diameter to clamp the head therein, wherein the pressure element comprises a first securing portion, and the receiving part comprises a second securing portion configured to engage the first securing portion, wherein when the head of the anchoring element is in the flexible portion of the pressure element and while the pressure element maintains a first rotational orientation relative to the receiving part, the pressure element is movable axially from the first end of the receiving part to a first axial position wherein the first securing portion of the pressure element is closer than the second securing portion of the receiving part is to the second end of the receiving part, and wherein when the pressure element is at the first axial position, the pressure element is rotatable between the first rotational orientation wherein the first securing portion is out of engagement with the second securing portion, and a second rotational orientation wherein the first securing portion is engaged with the second securing portion to form a rigid coupling therebetween to prevent removal of the pressure element from the first end of the receiving part, the method comprising:

assembling the bone anchoring device on the anchoring element;
inserting a shaft of the anchoring element into a bone;
adjusting an angular position of the bone anchoring device with respect to the anchoring element to be aligned with the rod;
inserting the rod into the channel;
advancing a fixation element in the channel towards the second end of the receiving part, the fixation element advancing the rod towards the second end, the rod advancing the pressure element towards the second end,
wherein the fixation element is advanced until the head is firmly clamped in the flexible portion of the pressure element and the relative positions of the rod and the anchoring element with respect to the bone anchoring device are locked.

15. The method of claim 14, wherein the assembling of the bone anchoring device on the anchoring element comprises:
inserting the pressure element into the receiving part from the first end;
rotating the pressure element from the first rotational orientation to the second rotational orientation to engage the first securing portion and the second securing portion; and
inserting the head of the anchoring element into the receiving part and the pressure element through the opening.

16. The method of claim 15, wherein the shaft of the anchoring element is inserted into the bone before the head of the anchoring element is inserted into the receiving part and the pressure element.

17. The method of claim 14, wherein the assembling of the bone anchoring device on the anchoring element comprises:
mounting the pressure element onto the head of the anchoring element;
inserting the anchoring element and the pressure element into the receiving part from the first end; and
rotating the pressure element from the first rotational orientation to the second rotational orientation to engage the first securing portion and the second securing portion.

18. A bone anchoring device comprising:
an anchoring element comprising a shaft for anchoring in a bone, and a head;
a receiving part comprising a first end and a second end, and having a channel for receiving a rod at the first end, and an accommodation space for accommodating the head, the accommodation space having an opening at the second end; and
a pressure element configured to be located at least partially in the accommodation space, the pressure element having first and second ends and comprising a flexible portion at the second end configured to be positioned around a portion of the head having a greatest diameter to clamp the head therein; and
wherein the anchoring element is pivotable with respect to the receiving part, and the pressure element is movable inside the accommodation space to lock the head within the flexible portion of the pressure element and to fix the anchoring element at an angle relative to the receiving part,
wherein the pressure element comprises a first securing portion spaced apart axially from the first and second ends of the pressure element, and the receiving part comprises a second securing portion configured to engage the first securing portion, and
wherein when the head of the anchoring element is in the flexible portion of the pressure element, the pressure element is insertable from the first end of the receiving part into the receiving part, and is rotatable between a first position wherein the first securing portion is out of engagement with the second securing portion, and a second position wherein the first securing portion is engaged with the second securing portion to form a rigid coupling therebetween to prevent removal of the pressure element from the first end of the receiving part.

19. The bone anchoring device according to claim 18, wherein the first and second securing portions comprise threaded sections provided at the pressure element and an inner wall of the receiving part, respectively, wherein in an engaged position, the pressure element is screwed into the accommodation space.

20. A bone anchoring device comprising:
an anchoring element comprising a shaft for anchoring in a bone, and a head;
a receiving part comprising a first end and a second end, and having two legs and a base defining a channel for receiving a rod at the first end, and an accommodation space for accommodating the head, the accommodation space having an opening at the second end; and
a pressure element configured to be located at least partially in the accommodation space, the pressure element comprising a flexible portion configured to be positioned around a portion of the head having a greatest diameter to clamp the head therein,
wherein the anchoring element is pivotable with respect to the receiving part, and the pressure element is movable inside the accommodation space to lock the head within the flexible portion of the pressure element and to fix the anchoring element at an angle relative to the receiving part, wherein the pressure element comprises a projection, and the receiving part has a securing portion configured to engage the projection and a recess on the base at a bottom of the channel, and wherein the pressure element is rotatable between a first rotational orientation wherein the projection is aligned with the recess and the pressure element is movable axially from the first end of the receiving part to an axial position where the projection is below the bottom of the channel in a direction towards the second end of the receiving part, and a second rotational orientation wherein the projection is engaged with the securing portion to form a rigid coupling therebetween to prevent removal of the pressure element from the first end of the receiving part.

* * * * *

UNITED STATES PATENT AND TRADEMARK OFFICE
CERTIFICATE OF CORRECTION

| | |
|---|---|
| PATENT NO. | : 9,486,246 B2 |
| APPLICATION NO. | : 12/969513 |
| DATED | : November 8, 2016 |
| INVENTOR(S) | : Lutz Biedermann et al. |

It is certified that error appears in the above-identified patent and that said Letters Patent is hereby corrected as shown below:

In the Claims

Column 8, Line 62, Claim 1        Delete "at the flat the",
                                                                   Insert --at the--

Signed and Sealed this
First Day of May, 2018

Andrei Iancu
*Director of the United States Patent and Trademark Office*